United States Patent
Huang

(10) Patent No.: US 6,425,144 B2
(45) Date of Patent: Jul. 30, 2002

(54) PROTECTIVE SPORTS EYEGLASSES WITH BUFFER AND SHOCK-ABSORBING FUNCTION

(76) Inventor: Ing Chung Huang, No. 218 Cheng Kung Three Road, Nantou City (TW)

( * ) Notice: Subject to any disclaimer, the term of this patent is extended or adjusted under 35 U.S.C. 154(b) by 0 days.

(21) Appl. No.: 09/785,201

(22) Filed: Feb. 20, 2001

Related U.S. Application Data

(63) Continuation of application No. 09/377,731, filed on Aug. 19, 1999, now Pat. No. 6,195,808, which is a continuation of application No. 08/876,492, filed on Jun. 16, 1997, now Pat. No. 5,950,247.

(30) Foreign Application Priority Data

Jun. 15, 1996 (TW) ........................................ 85107202 A

(51) Int. Cl.[7] .................................................. A61F 9/02
(52) U.S. Cl. .......................................................... 2/431
(58) Field of Search ............................ 2/431, 440, 426, 2/428, 430, 432, 439, 442; 128/858

(56) References Cited

U.S. PATENT DOCUMENTS

| | | | | |
|---|---|---|---|---|
| 2,393,533 A | * | 1/1946 | Heinz .............................. | 2/440 |
| 3,725,953 A | * | 4/1973 | Johnson et al. .............. | 2/430 X |
| 4,286,340 A | * | 9/1981 | Lathrop .......................... | 2/430 |
| 5,129,109 A | * | 7/1992 | Runckel ......................... | 2/426 |
| 5,651,146 A | * | 7/1997 | Chao .............................. | 2/452 |

* cited by examiner

*Primary Examiner*—Peter Nerbun
(74) *Attorney, Agent, or Firm*—Bacon & Thomas, PLLC

(57) ABSTRACT

Protective sports eyeglasses with a buffer being a shock-absorbing function includes a cushion having a hollow sealed endless shape. The cushion has a 3D tubular space instead of 2D (two dimensions) surface. The cushion is attached on an annular edge of a lens contacting the face of a wearer so as to fit the curvature of the face, and has an inner pressure preset in advance so that the cushion may contact closely and comfortably the face of a wearer with a buffer and a shock-absorbing effect.

9 Claims, 4 Drawing Sheets

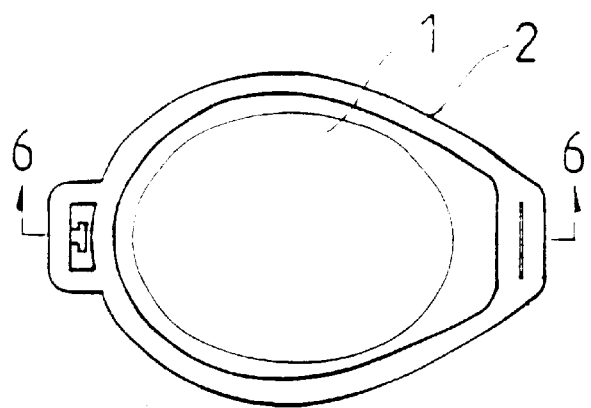
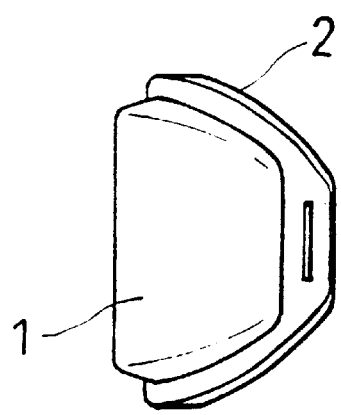
FIG.1  FIG.2
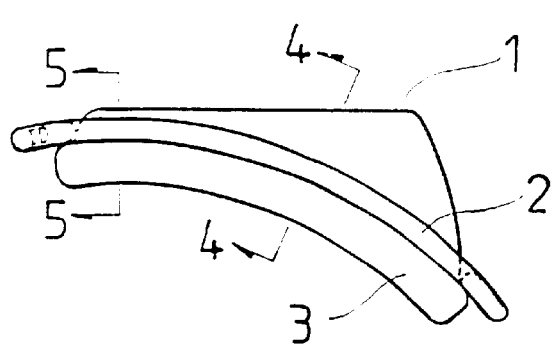
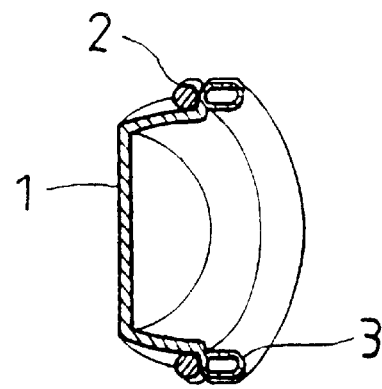
FIG.3  FIG.4
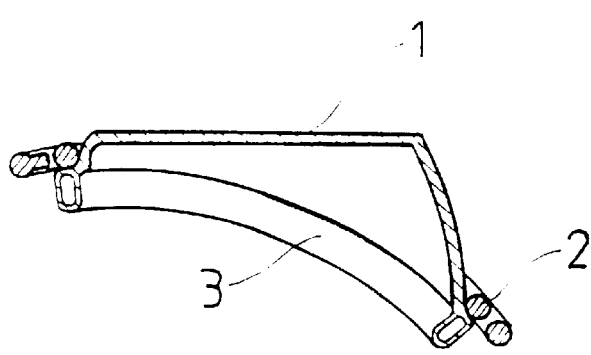
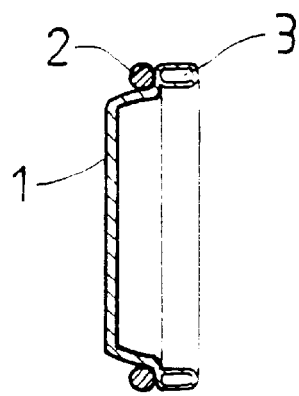
FIG.6  FIG.5

PROTECTIVE SPORTS EYEGLASSES WITH BUFFER AND SHOCK-ABSORBING FUNCTION

CROSS REFERENCE TO RELATED APPLICATION

This application is a continuation of non-provisional application serial No. 09/377,731, filed Aug. 19, 1999, U.S. Pat. No. 6,195,808 which is a continuation of non-provisional application serial number 08/876,492, filed Jun. 16, 1997 U.S. Pat. No. 5,950,247.

BACKGROUND OF THE INVENTION

Common conventional protective eyeglasses such as those used in swimming, diving, cycling, etc. generally have a cushion made of an elastic material such as a sponge or foam rubber to produce soft and comfortable feeling in wearing it on a face.

However, when conventional protective eyeglasses receive a strike or shock, a wearer may suffer pain, harm or wound because of poor elasticity that the cushions have, the elasticity limited by its thickness and its elasticity coefficient.

SUMMARY OF THE INVENTION

In view of the aforesaid disadvantages of the conventional protective eyeglasses, this invention has been devised to offer protective sports eyeglasses with buffer and shock-absorbing functions, which have a cushion containing a hollow 3D space attached with a frame or a lens so as to produce soft and comfortable feeling when wearing it.

BRIEF DESCRIPTION OF THE DRAWINGS

This invention will be better understood by referring to the accompanying drawings, wherein:

FIG. 1 is a front view of a first preferred embodiment of eyeglasses with buffer and shock-absorbing functions in the present invention;

FIG. 2 is a right side view of FIG. 1;

FIG. 3 is a bottom view of FIG. 1;

FIG. 4 is a cross-sectional view of line 4—4 in FIG. 3;

FIG. 5 is a cross-sectional view of line 5—5 in FIG. 3;

FIG. 6 is a cross-sectional view of line 6—6 in FIG. 1;

DETAILED DESCRIPTION OF THE PREFERRED EMBODIMENT

A first preferred embodiment of protective sports eyeglasses with buffer and shock-absorbing functions in the present invention, as shown in FIGS. 1–6, includes a lens 1 and a frame 2 independent from each other and able to be firmly combined together. Further, a cushion 3 is provided with the lens 1 on the side contacting with the face of a wearer, formed integral with the lens at its peripheral edge, and having a hollow interior. The cushion 3 is shaped as an annular hollow 3D ring that is sealed. Further, the cushion 3 is filled at a preset pressure, permitting it to contact the face of a wearer steadily and comfortably because of 3D curvature of the cushion 3, having a buffer and shock-absorbing effect. The cushion 3 is made of materials having high density and low percolation, selected from polyimide, polyethylene, polypropelene, acetic salt of ethylene, polyester, polyamide, ployurethane, chlorinated polyethylene, or butyl rubber. Materials may be used having good elasticity, flexibility, anti-low-temperature, and which can be processed easily.

A second preferred embodiment of the protective sports eyeglasses with buffer and shock-absorbing function in the present invention is shown in FIGS. 7–11. It includes a lens 1 and a frame 2 formed integral with the lens 1, and a cushion 3 made independent to be attached on the frame 2. The cushion 3 is an annular hollow 3D ring with a preset curvature. The hollow interior of the cushion 3 is filled at air pressure of a preset value. The frame 2 has an annular groove 21 of a preset size for the cushion 3 to fit therein with close fitness and stability.

Figure 7:
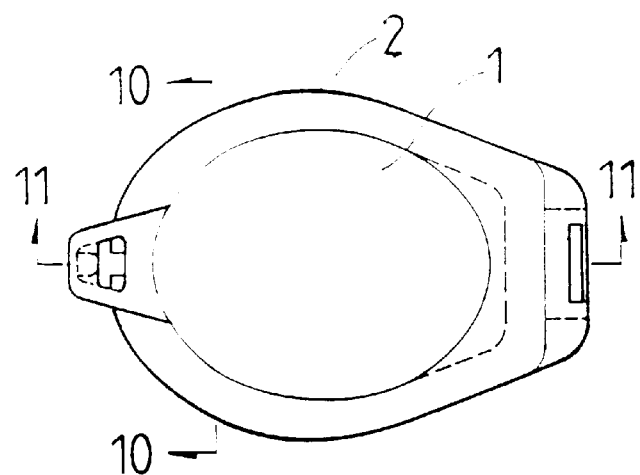
FIG. 7 is a front view of a second preferred embodiment of eyeglasses with buffer and shock-absorbing function in the present invention.
Figure 8:
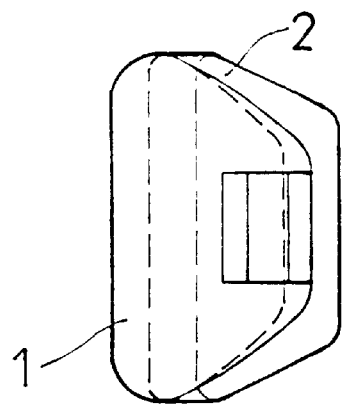
FIG. 8 is a right side view of FIG. 7.
Figure 9:
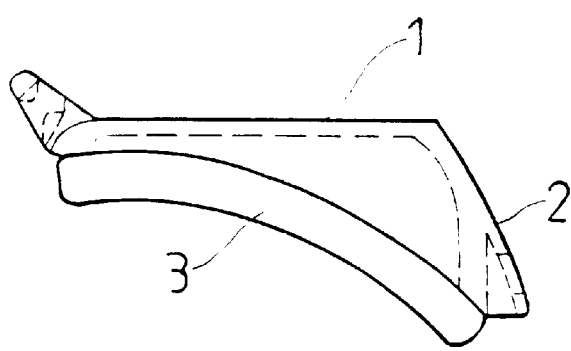
FIG. 9 is a bottom view of FIG. 7.
Figure 10:
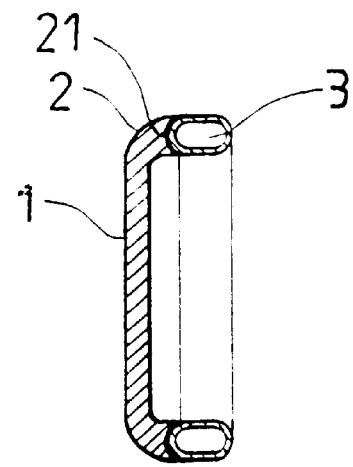
FIG. 10 is a cross-sectional view of line 10—10 in FIG. 7.
Figure 11:
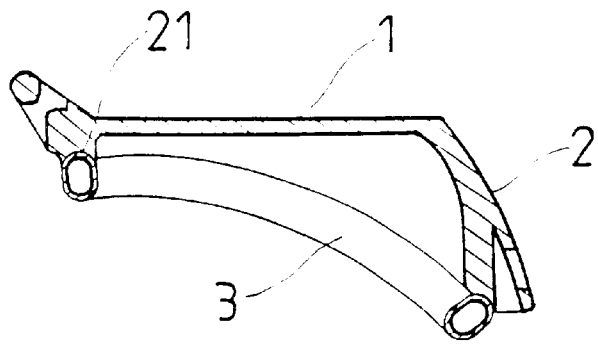
FIG. 11 is a cross-sectional view of line 11—11 in FIG. 7.
Figure 12:
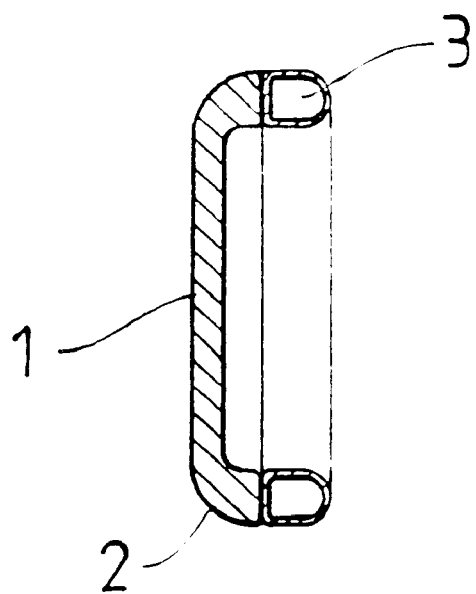
FIG. 12 is a cross-sectional view of another preferred embodiment of FIG. 10.
Figure 13:
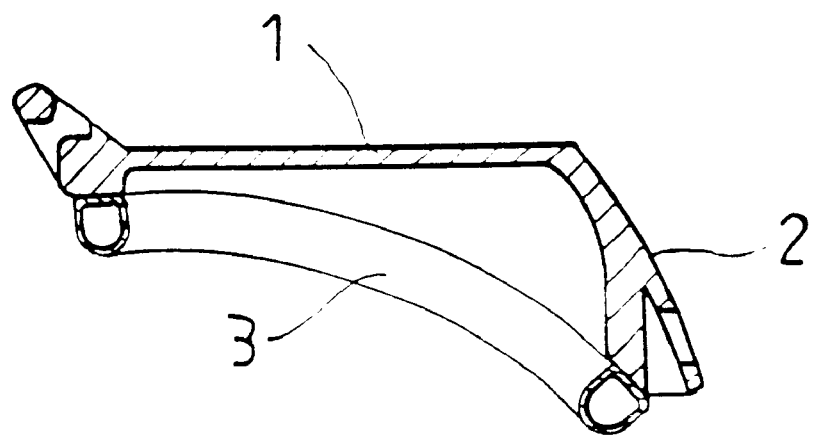
FIG. 13 is a cross-sectional view of another preferred embodiment of FIG. 11.

Another preferred embodiment is shown in FIGS. 12 and 13. It includes a lens I, a frame 2 having a flat surface without an annular groove 21. The annular flat surface of the frame 2 should be wide enough for attaching the cushion 3 thereon.

The cross-section of an inner or an outer shape at any point of the hollow 3D cushion 3 is all the same or not the same, of any geometric shape. As the cushion 3 is made to have a hollow 3D shape closely contacting the face of a user, and a preset pressure in the hollow interior to minimize sport harm or wound with its buffer and shock-absorbing function in practical use, thus protecting the face from being hurt.

Figure 14:
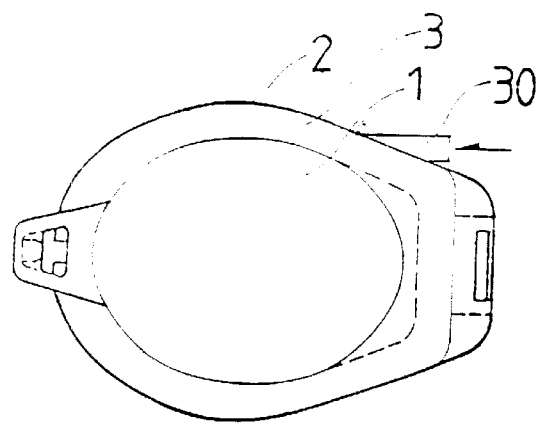
FIG. 14 is a front view of a cushion provided with a hollow passageway in the protective sports eyeglasses in the present invention.
Figure 15:
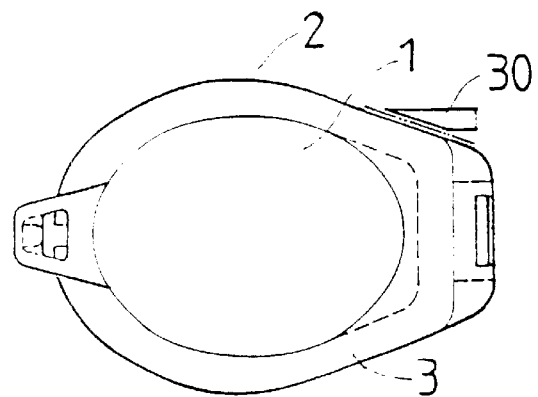
FIG. 15 is a front view of the hollow passageway cut after the cushion is inflated in the present invention; and, FIG. 16 is a front view of an air valve attached on the hollow passageway fIXed with the cushion in the present invention.
Figure 16:
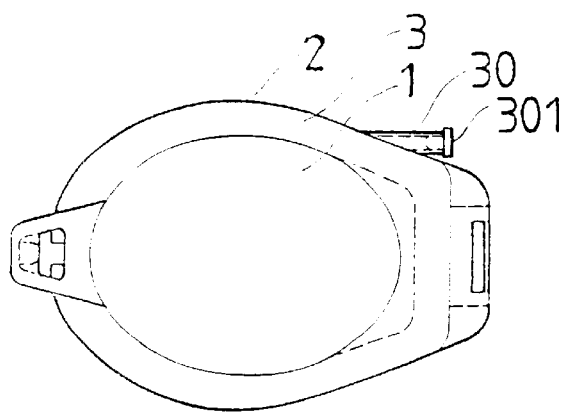

The inner buffer pressure filled in the cushion 3 may be preferably on the order of 0–40 psi, and then different buffer pressure can be selected for different objects and different conditions, able to be chosen by consumers. So at least one hollow passageway 30 maybe added to the cushion 3, communicating the cushion 3 with outer air, as shown in FIGS. 14–16, for connecting an air valve 301, a valve, a pump, or the like so as to fill the hollow interior of the cushion 3 with a gas, a semi-fluid, a fluid, a liquid or low-percolating large particle gas such as SF6, C2F6, etc.

An inner pressure of the cushion 3 not communicating with outer air is produced with a special method, such as a process with a hollow mold placed in an air pressure container, forming a sealed cushion 3 with the same inner pressure as that in the air pressure container, which is preset in advance.

While the preferred embodiments of the invention have been described above, it will be recognized and understood that various modifications may be made therein and the appended claims are intended to cover all such modifications which may fall within the spirit and scope of the invention.

What is claimed is:

1. Protective sport eyeglasses configured to be worn on a face of a user and comprising:

a) a frame defining at least one eye opening;

b) a lens on the frame and at least partially covering the at least one eye opening and one of the frame and lens including an inwardly facing mounting surface; and c) a pad having an outwardly facing mounting surface attached to the inwardly facing mounting surface of one of the frame and lens so as to contact the face of a user to provide sealing or shock-absorbing functions during use, said pad being a molded annular hollow three-dimensional cushion that is non-releasably filled to a predetermined pressure with a fluid material and having a preset curvature formed as an integral unit with said lens and said frame, the three-dimensional preset curvature of the cushion being maintained whether or not the cushion is filled with the fluid material.

2. Protective sport eyeglasses configured to be worn on a face of a user and comprising:

a) a lens for at least partially covering at least one eye opening, the lens including an inwardly facing mounting surface; and b) a pad having an outwardly facing mounting surface attached to the inwardly facing mounting surface of the lens for contacting the face of a user to provide sealing or shock-absorbing functions during use, said pad being molded as an integral unit with said lens; and said pad being an annular hollow three-dimensional cushion that is non-releasably filled to a predetermined pressure with a fluid material and having a preset curvature that is maintained whether or not the cushion is filled with the fluid material.

3. A fluid cushion pad for protective sport eyeglasses of claim 2, wherein the cushion includes at least one hollow tube extending therefrom for inflating the cushion.

4. A fluid cushion pad for protective sport eyeglasses of claim 2, further including a pump for inflating said cushion.

5. A fluid cushion pad for protective sport eyeglasses of claim 4, further including a valve.

6. A fluid cushion pad for protective sport eyeglasses of claim 2, wherein the hollow, sealed cushion is made from a high density, low-percolation material.

7. A fluid cushion pad for protective sport eyeglasses of claim 6, wherein the high density, low percolation material is a material selected from the group consisting of polyamide, polyethylene, polypropylene, ethylene, acetic salt of ethylene, polyester, polyamide, polyurethane, chlorinated polyethylene, butyl rubber and mixtures thereof.

8. Protective sport eyeglasses configured to be worn on a face of a user and comprising:

a) a frame defining at a least one eye opening;

b) a lens on the frame and at least partially covering the at least the one eye opening and one of the frame and lens including an inwardly facing mounting surface; and c) a pad having an outwardly facing mounting surface attached to the inwardly facing mounting surface of one of the frame and lens so as to contact the face of a user to provide sealing or shock-absorbing functions during use, said pad being an annular hollow-sealed three-dimensional fluid cushion that is non-releasably filled to a predetermined pressure with a low-percolating large particle gas, the cushion having a preset curvature and is formed as an integral unit with said lens and said frame.

9. Protective sport eyeglasses configured to be worn on a face of a user and comprising:

a) a frame defining at least one eye opening;

b) a lens on the frame and at least partially covering the at least the one eye opening and one of the frame and lens including an inwardly facing mounting surface; and c) a pad having an outwardly facing mounting surface attached to the inwardly facing mounting surface of one of the frame and lens so as to contact the face of a user to provide sealing or shock-absorbing functions during use, said pad being an annular hollow-sealed three-dimensional fluid cushion that is non-releasably filled to a predetermined pressure with a liquid, the cushion having a preset curvature and is formed as an integral unit with said lens and said frame.

* * * * *